(12) United States Patent
Ahlers et al.

(10) Patent No.: US 6,753,450 B2
(45) Date of Patent: Jun. 22, 2004

(54) PROCESS FOR THE PREPARATION OF ALDEHYDES

(75) Inventors: Wolfgang Ahlers, Worms (DE); Michael Slany, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/275,563

(22) PCT Filed: May 11, 2001

(86) PCT No.: PCT/EP01/05406

§ 371 (c)(1),
(2), (4) Date: Nov. 7, 2002

(87) PCT Pub. No.: WO01/85662

PCT Pub. Date: Nov. 15, 2001

(65) Prior Publication Data

US 2003/0114714 A1 Jun. 19, 2003

(30) Foreign Application Priority Data

May 12, 2000 (DE) .......................... 100 23 470

(51) Int. Cl.⁷ .............................................. C07C 45/50
(52) U.S. Cl. ........................ 568/454; 568/451; 568/452
(58) Field of Search ................................ 568/454, 451, 568/452

(56) References Cited

U.S. PATENT DOCUMENTS 6,156,934 A * 12/2000 Suykerbuyk et al. ......... 568/12

FOREIGN PATENT DOCUMENTS

WO    98/42717    10/1998

\* cited by examiner

*Primary Examiner*—Johann Richter
*Assistant Examiner*—Sikarl A. Witherspoon
(74) *Attorney, Agent, or Firm*—Keil & Weinkauf

(57) ABSTRACT

The invention relates to a process for the preparation of aldehydes in which at least one compound containing a vinyl or vinylidene group is reacted with carbon monoxide and hydrogen in the presence of a source of a metal from sub-group VIII and in the presence of a bidentate diphosphine ligand, where the diphosphine ligand has the general formula I

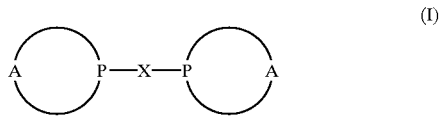

in which A together with the phosphorus atom to which it is bonded, in each case forms a 2-phosphatricyclo [3.3.1.1{3,7}]decyl radical, in which one or more non-adjacent carbon atoms may be replaced by oxygen atoms and which is substituted or unsubstituted, and X is a bridging chain having 1 to 10 carbon atoms, and the molar ratio between the diphosphine ligand and the metal is at least 5. The process gives predominantly n-aldehydes.

8 Claims, No Drawings

PROCESS FOR THE PREPARATION OF ALDEHYDES

The present invention relates to a process for the preparation of aldehydes in which at least one compound containing a vinyl or vinylidene group is reacted with carbon monoxide and hydrogen in the presence of a source of a metal from sub-group VIII and in the presence of a bidentate diphosphine ligand.

Hydroformylation or the oxo synthesis is an important large-scale industrial process and serves for the preparation of aldehydes by reaction of ethylenically unsaturated compounds with carbon monoxide and hydrogen. The reaction itself is highly exothermic and generally proceeds under superatmospheric pressure and at elevated temperatures in the presence of catalysts. The catalysts employed are usually metals from sub-group VIII of the Periodic Table of the Elements, in particular cobalt, rhodium, iridium, ruthenium, palladium or platinum compounds or complexes, which may have been modified by means of nitrogen- or phosphorus-containing ligands in order to influence the activity and/or selectivity.

In the case of asymmetrical ethylenically unsaturated compounds, the two possible orientations of the carbon monoxide adduction onto the C—C double bond give different aldehydes. In general, therefore, a mixture of isomeric aldehydes is obtained, as illustrated below.

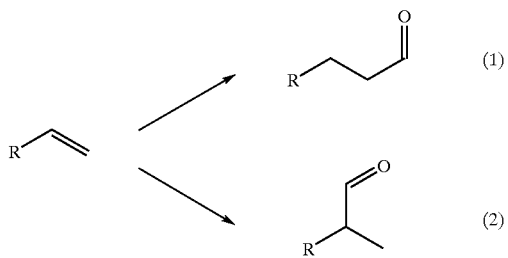

The compound (1) is frequently known as n-aldehyde, and the compound (2) as iso-aldehyde.

Owing to the fact that the n-aldehydes are generally of significantly greater industrial importance than the isoaldehydes, it is an aim to optimize the hydroformylation catalysts and conditions in order to achieve the greatest possible n-selectivity, i.e. the highest possible ratio of n-aldehyde to isoaldehyde in the product aldehydes.

WO 98/42717 describes carbonylation reactions in the presence of a carbonylation catalyst containing a diphosphine, of which at least one phosphorus atom is part of a 2-phosphatricyclo[3.3.1.1{3,7}]decyl group. The carbonylation reactions described also include hydroformylations. Although WO 98/42717 indicates that, in order to prepare the catalyst system described therein, the ligand is generally employed in excess relative to the metal cation, nothing is stated regarding the amount of ligand present during the carbonylation reaction. In the hydroformylation examples in WO 98/42717, molar ratios between the diphosphine ligand and the rhodium metal of 1:1.2 (Example 9), 1:1 (Example 10) and 1:2 (Example 11) are used. In the hydroformylation of propene, an approximately equimolar mixture of butanal and 2-methylpropanal is obtained.

It is an object of the present invention to indicate a process with very high n-selectivity for the preparation of aldehydes by hydroformylation of compounds containing at least one vinyl or vinylidene group.

We have found that this object is achieved by a process for the preparation of aldehydes in which at least one compound containing a vinyl or vinylidene group is reacted with carbon monoxide and hydrogen in the presence of a source of a metal from sub-group VIII and in the presence of a bidentate diphosphine ligand, where the diphosphine ligand has the general formula I

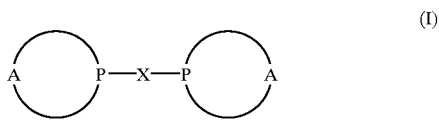

in which
A together with the phosphorus atom to which it is bonded, in each case forms a 2-phosphatricyclo[3.3.1.1{3,7}]decyl radical, in which one or more non-adjacent carbon atoms may be replaced by oxygen atoms and which is substituted or unsubstituted, and
X is a bridging chain having 1 to 10 carbon atoms, and the molar ratio between the diphosphine ligand and the metal is at least 5.

The molar ratio between the diphosphine ligand and the metal is in accordance with the invention at least 5, preferably at least 8 and in particular at least about 10. The molar ratio is generally less than about 50, usually less than about 20.

Tricyclo[3.3.1.1{3,7}]decane is also known by the trivial name "adamantane". In the 2-phosphatricyclo[3.3.1.1{3,7}] decyl radical of the ligand used in accordance with the invention, one or more non-adjacent carbon atoms, which are preferably not adjacent to the phosphorus atom, may have been replaced by oxygen atoms. The carbon atoms in positions 6, 9 and 10 have preferably been replaced by oxygen atoms.

The 2-phosphatricyclo[3.3.1.1{3,7}]decyl radical may carry substituents on one or more of its carbon atoms. One or more carbon atoms in positions 1, 3, 5 and/or 7, in particular all carbon atoms in positions 1, 3, 5 and 7, preferably carry substituents, which are preferably identical. Examples of suitable substituents are alkyl, cycloalkyl, haloalkyl, aryl and aralkyl. The carbon atoms in positions 4 and/or 8 may carry one or two substituents, such as $C_1$–$C_4$-alkyl or halogen atoms, in particular fluorine atoms.

The two 2-phosphatricyclo[3.3.1.1{3,7}]decyl radicals present in the diphosphine ligands to be used in accordance with the invention may have identical or different substituents. Depending on the substitution pattern, the diphosphines may be in the form of diastereomers. In general, both the diastereomer mixtures and the pure diastereomers are suitable for the purposes according to the invention.

X is a bridging chain having 1 to 10 atoms, preferably 2 to 4 atoms, in particular 3 atoms. X is preferably a $C_1$- to $C_{10}$-alkylene bridge, which may have one, two, three or four double bonds and/or may be interrupted by one, two or three non-adjacent heteroatoms and/or may be fused to one, two or three saturated or unsaturated 3- to 7-membered carbocyclic or heterocyclic rings.

The fused unsaturated carbocyclic rings in radical X are preferably benzene or naphthalene, in particular benzene. Fused benzene rings are preferably unsubstituted or have 1, 2 or 3, in particular 1 or 2, substituents selected from alkyl, alkoxy, halogen, haloalkyl, nitro, carboxyl, alkoxycarbonyl and cyano. Fused saturated carbocyclic rings are preferably cyclopropyl, cyclobutyl, cyclopentyl or cyclohexyl.

If the alkylene bridge in radical X is interrupted by heteroatoms, these are preferably selected from oxygen, sulfur and nitrogen.

Preferred radicals X are selected from

—(CH$_2$)$_x$—

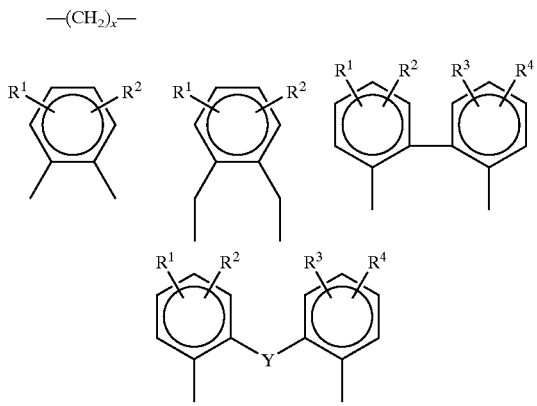

where x is an integer from 1 to 10, preferably 2 to 4,

Y is O, S or NR$^5$, where R$^5$ is alkyl, cycloalkyl or aryl, or Y is a C$_1$–C$_3$-alkylene bridge, which may have a double bond and/or an alkyl, cycloalkyl or aryl substituent, or Y is a C$_2$–C$_3$-alkylene bridge which is interrupted by O, S or NR$^5$, R$^1$, R$^2$, R$^3$ and R$^4$, independently of one another, are hydrogen, alkyl, cycloalkyl, haloalkyl, aryl, alkoxy, aryloxy, aralkoxy, halogen, nitro, alkoxycarbonyl or cyano.

X is particularly preferably propylene.

A, together with the phosphorus atom to which it is bonded, is preferably a group of the general formula II

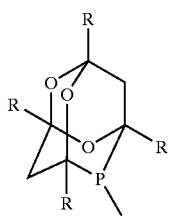

(II)

where the radicals R, independently of one another, are alkyl, cycloalkyl, haloalkyl, aryl or aralkyl.

For the purposes of the present invention, the terms used have the following meanings, unless stated otherwise:

"alkyl" means straight-chain or branched alkyl, preferably C$_1$–C$_{20}$-alkyl, in particular C$_1$–C$_8$-alkyl, particular preferably C$_1$–C$_4$-alkyl. Examples of alkyl groups are, in particular, methyl, ethyl, propyl, isopropyl, n-butyl, 2-butyl, s-butyl, t-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl and octyl;

"cycloalkyl" preferably means C$_5$–C$_7$-cycloalkyl, such as cyclopentyl, cyclohexyl or cycloheptyl;

"haloalkyl" preferably means C$_1$–C$_4$-haloalkyl, i.e. a C$_1$–C$_4$-alkyl radical which is partially or fully substituted by fluorine, chlorine, bromine and/or iodine, such as chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromethyl, 2-iodoethyl, 2,2-difluoroethyl, 2,2,2-trifluoroethyl, 2-chloro-2-fluoroethyl, 2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

"aryl" preferably means C$_6$–C$_{16}$-aryl, such as phenyl, tolyl, xylyl, mesityl, naphthyl, anthracenyl, phenanthrenyl, naphthacenyl; in particular phenyl or naphthyl;

"aralkyl" preferably means C$_7$–C$_{20}$-aralkyl, in particular phenyl-C$_1$–C$_4$-alkyl, such as benzyl or phenethyl;

"alkoxy" preferably means C$_1$–C$_{20}$-alkoxy containing an alkyl group, preferably as defined above;

"cycloalkoxy" preferably means C$_5$–C$_7$-cycloalkoxy containing a cycloalkyl group, preferably as defined above;

"aryloxy" preferably means C$_7$–C$_{16}$-aryloxy containing an aryl group, preferably as defined above;

"aralkoxy" preferably means C$_7$–C$_{20}$-aralkoxy containing an aralkyl group, preferably as defined above;

and "halogen" means fluorine, chlorine, bromine or iodine, preferably fluorine or chlorine.

The radicals R, independently of one another, are particularly preferably C$_1$–C$_4$-alkyl, C$_1$–C$_4$-haloalkyl or phenyl, in particular methyl, t-butyl, trifluoromethyl or phenyl.

Particular preferred ligands include 1,2-P,P'-di(2-phospha-1,3,5,7-tetramethyl-6,9,10-trioxatricyclo-[3.3.1.1{3,7}]decyl)ethane, 1,3-P,P'-di(2-phospha-1,3,5,7-tetramethyl-6,9,10-trioxatricyclo-[3.3.1.1{3,7}]decyl)propane and 1,6-P,P'-di(2-phospha-1,3,5,7-tetramethyl-6,9,tetramethyl-6,9,10-trioxatricyclo[3.3.1.1{3,7}]decyl)hexane.

In order to prepare the diphosphine ligands of the formula I, a compound containing 2 primary phosphine groups can, for example, be reacted with a 1,3-diketone, for example 2,4-pentanedione or substituted 2,4-pentanediones, such as perfluoro-2,4-pentanedione or 1,1,1,5,5,5-hexafluoro-2,4-pentanedione, with acid catalysis. The compounds of the formula I are generally obtained in high purity and can be used directly without further purification. With respect to suitable reaction conditions, reference is made to J. Am. Chem. Soc. 1961, Vol. 83, 3279–3282 and Chem. Com. 1999 (10, 1901–902) and WO 98/42717.

Im general, catalytically active species of the general formula H$_x$M$_y$(CO)$_z$L$_q$, in which M is a metal from subgroup VIII of the Periodic Table, L is a ligand of the general formula I, and q, x, y and z are integers depending on the valency and type of the metal, are generally formed from the catalysts or catalyst precursors employed under hydroformylation conditions. The complexes may, if desired, additionally contain further ligands, which are preferably selected from halides, amines, carboxylates, acetylacetonate, aryl- and alkylsulfonates, olefins, dienes, cycloolefins, nitriles, nitrogen-containing heterocyclic compounds, aromatic compounds and heteroaromatic compounds, ethers, $PF_3$, and monodentate, bidentate and polydentate phosphine, phosphinite, phosphonite and phosphite ligands which do not conform to the formula I.

The metal from sub-group VIII is preferably cobalt, ruthenium, rhodium, nickel, palladium, platinum, osmium or iridium and in particular cobalt, ruthenium, iridium, rhodium, nickel, palladium or platinum. Rhodium is the most preferred. Suitable sources of said metals are generally their compounds, for example salts, or complexes.

According to a preferred embodiment, the hydroformylation catalysts are prepared in situ in the reactor employed for the hydroformylation reaction. If desired, however, the ligand/metal complexes can also be prepared separately and isolated by conventional methods. For in-situ preparation, it is possible, for example, to react at least one ligand of the formula I, a compound or a complex of the metal from sub-group VIII, if desired at least one further ligand and if desired an activator with carbon monoxide and hydrogen in an inert solvent under hydroformylation conditions.

Examples of suitable rhodium compounds or complexes are rhodium(II) and rhodium(III) salts, such as rhodium(III) chloride, rhodium(III) nitrate, rhodium(III) sulfate, potassium rhodium sulfate, rhodium(II) or rhodium(III) carboxylates, such as rhodium(II) and rhodium(III) acetate, rhodium(III) oxide, salts of rhodium(III) acid, trisammonium hexachlororhodate(III), etc. Also suitable are rhodium complexes, such as rhodium biscarbonylacetylacetonate, acetylacetonatobisethylenerhodium(I), etc. Preference is given to rhodium biscarbonylacetylacetonate, rhodium acetate and rhodium ethylhexanoate.

Likewise suitable are ruthenium salts or compounds. Examples of suitable ruthenium salts are ruthenium(III) chloride, ruthenium(IV), ruthenium(VI) and ruthenium (VIII) oxide, alkali metal salts of ruthenium oxygen acids, such as $K_2RuO_4$ or $KRuO_4$, or complex compounds, such as $RuHCl(CO)(PPh_3)_3$. It is also possible to use the metal carbonyls of ruthenium, such as trisruthenium dodecacarbonyl or hexaruthenium octadecacarbonyl, or mixed forms in which some of the CO has been replaced by triorganophosphines, such as $Ru(CO)_3(PPh_3)_2$.

Examples of suitable cobalt compounds are cobalt(II) chloride, cobalt(II) sulfate, cobalt(II) carbonate, cobalt(II) nitrate, the amine and hydrate complexes thereof, cobalt carboxylates, such as cobalt formate, cobalt acetate, cobalt ethylhexanoate, cobalt naphthanoate, and cobalt/caprolactamate complex. Here too, it is possible to use the carbonyl complexes of cobalt, such as dicobalt octacarbonyl, tetracobalt dodecacarbonyl and hexacobalt hexadecacarbonyl.

The above and other suitable compounds of cobalt, rhodium, ruthenium and iridium are known in principle and are described adequately in the literature or can be prepared by the person skilled in the art analogously to the compounds that are already known.

Examples of suitable activators are Brödnsted acids, Lewis acids, such as $BF_3$, $AlCl_3$ and $ZnCl_2$, and Lewis bases.

Suitable substrates for the process according to the invention are in principle all compounds which contain one or more vinyl or vinylidene groups. These include, for example, $C_3$–$C_{20}$-α-alkenes, in particular linear $C_3$–$C_{20}$-α-alkenes, such as propene, 1-butene, 1-pentene, 1-hexene, 1-heptene, 1-octene, 1-nonene, 1-decene, 1-undecene, 1-dodecene, etc. A further preferred starting material is isobutene.

Other preferred starting materials are ω-nitrilo-$C_2$–$C_{20}$-alkenes, such as acrylonitrile and 4-pentene nitrile; and ω-alkoxycarbonyl-$C_2$–$C_{20}$-alkenes, such as alkyl acrylates and alkyl 4-pentenoates. Also suitable are vinyl aromatic compounds, such as styrene and vinylpyridine.

The hydroformylation reaction can be carried out continuously, semi-continuously or batchwise. Suitable reactors are known to the person skilled in the art and are described, for example, in Ullmann's Enzyklopädie der technischen Chemie, Volume 1, 3rd Edition, 1951, pp. 743 ff.

Carbon monoxide and hydrogen are usually employed in the form of a mixture, so-called synthesis gas. The molar ratio between carbon monoxide and hydrogen is generally from about 5:95 to 70:30, preferably from about 40:60 to 60:40. In particular, a molar ratio between carbon monoxide and hydrogen in the region of about 1:1 is employed.

The temperature during the hydroformylation reaction is generally in the range from about 80 to 180° C., preferably from about 100 to about 160° C. The reaction is generally carried out at the partial pressure of the reaction gas at the selected reaction temperature. In general, the pressure is in the range from about 5 to 200 bar, in particular from 5 to 30 bar. The optimum temperature and the optimum pressure are dependent on the unsaturated compound employed.

The catalytically active ligand/metal complexes can be separated off from the hydroformylation reaction product by conventional methods known to the person skilled in the art and can generally be re-employed for the hydroformylation, if necessary after work-up.

In the hydroformylation, solvents can be used concomitantly, such as the high-boiling secondary-reaction products of the aldehydes formed in the hydroformylation. Other suitable solvents are aromatic hydrocarbons, such as toluene and xylene, aliphatic hydrocarbons, ethers, such as 2,5,8-trioxanonane, diethyl ether and anisole, sulfones, such as sulfolane, or esters, such as 3-hydroxy-2,2,4-trimethylpentyl 1-isobutyrate (Texanol).

By means of the process according to the invention, n-selectivities of greater than 80%, in particular greater than 90%, are generally achieved. The invention is illustrated in greater detail by the following, non-restrictive examples:

EXAMPLES

The ligands were synthesized as described in WO 98/42717. The abbreviation "acac" stands for acetylacetonate; L:M stands for the molar ratio between the ligand and metal. The reaction mixtures obtained in the examples were analyzed by gas chromatography (GC).

Comparative Example 1

Hydroformylation of 1-octene using 1,3-P,P'-di(2-phospha-1,3,5,7-tetramethyl-6,9,10-trioxatricyclo [3.3.1.1{3,7}]decylpropane 0.9 mg of $Rh(CO)_2acac$ and 1.65 mg of 1,3-P,P'-di(2-phospha-1,3,5,7-tetramethyl-6,9,10-trioxatricyclo [3.3.1.1{3,7}]-decylpropane (60 ppm of Rh, L:M 1:1) were dissolved separately in a total of 3 g of toluene, mixed and aerated at 100° C. with 10 bar of synthesis gas ($CO:H_2$=1:1). After 30 minutes, the pressure was released, 3 g of 1-octene were added, and the mixture was hydroformylated for 4 hours at 100° C. and 10 bar. The conversion was 94%, the aldehyde selectivity was 11%, the internal olefin selectivity was 89%. The molar ratio between n-nonanal and isononanal was 45:55.

Comparative Example 2

Hydroformylation of 1-octene using 1,3-P,P'-di(2-phospha-1,3,5,7-tetramethyl-6,9,10-trioxatricyclo [3.3.1.1{3,7}]decylpropane 0.9 mg of $Rh(CO)_2acac$ and 2.47 mg of 1,3-P,P'-di(2-phospha-1,3,5,7-tetramethyl-6,9,10-trioxatricyclo

[3.3.1.1{3,7}]-decylpropane (60 ppm of Rh, L:M=1.5:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 83%, the aldehyde selectivity was 12%, the internal olefin selectivity was 88%. The molar ratio between n-nonanal and isononanal was 43:57.

Comparative Example 3

Hydroformylation of 1-octene using 1,3-P,P'-di(2-phospha-1,3,5,7-tetramethyl-6,9,10-trioxatricyclo [3.3.1.1{3,7}]decylpropane 0.9 mg of Rh(CO)$_2$acac and 3.3 mg of 1,3-P,P'-di(2-phospha-1,3,5,7-tetramethyl-6,9,10-trioxatricyclo [3.3.1.1{3,7}]-decylpropane (60 ppm of Rh, L:M=2:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 83%, the aldehyde selectivity was 10%, the internal olefin selectivity was 90%. The molar ratio between n-nonanal and isononanal was 44:56.

Comparative Example 4

Hydroformylation of 1-octene using 1,3-P,P'-di(2-phospha-1,3,5,7-tetramethyl-6,9,10-trioxatricyclo [3.3.1.1{3,7}]decylpropane 0.9 mg of Rh(CO)$_2$acac and 4.9 mg of 1,3-P,P'-di(2-phospha-1,3,5,7-tetramethyl-6,9,10-trioxatricyclo [3.3.1.1{3,7}]-decylpropane (60 ppm of Rh, L:M=3:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 85%, the aldehyde selectivity was 27%, the internal olefin selectivity was 73%. The molar ratio between n-nonanal and isononanal was 72:28.

Comparative Example 5

Hydroformylation of 1-octene using 1,3-P,P'-di(2-phospha-1,3,5,7-tetramethyl-6,9,10-trioxatricyclo [3.3.1.1{3,7}]decylpropane 0.9 mg of Rh(CO)$_2$acac and 6.6 mg of 1,3-P,P'-di(2-phospha-1,3,5,7-tetramethyl-6,9,10-trioxatricyclo [3.3.1.1{3,7}]-decylpropane (60 ppm of Rh, L:M=4:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 85%, the aldehyde selectivity was 25%, the internal olefin selectivity was 75%. The molar ratio between n-nonanal and isononanal was 75:25.

Example 6

Hydroformylation of 1-octene using 1,3-P,P'-di(2-phospha-1,3,5,7-tetramethyl-6,9,10-trioxatricyclo [3.3.1.1{3,7}]decylpropane 0.9 mg of Rh(CO)$_2$acac and 8.2 mg of 1,3-P,P'-di(2-phospha-1,3,5,7-tetramethyl-6,9,10-trioxatricyclo [3.3.1.1{3,7}]-decylpropane (60 ppm of Rh, L:M=5:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 100%, the aldehyde selectivity was 69%, the internal olefin selectivity was 31%. The molar ratio between n-nonanal and isononanal was 97:3.

Example 7

Hydroformylation of 1-octene using 1,3-P,P'-di(2-phospha-1,3,5,7-tetramethyl-6,9,10-trioxatricyclo [3.3.1.1{3,7}]decylpropane 0.9 mg of Rh(CO)$_2$acac and 16.4 mg of 1,3-P,P'-di(2-phospha-1,3,5,7-tetramethyl-6,9,10-trioxatricyclo [3.3.1.1{3,7}]-decylpropane (60 ppm of Rh, L:M=10:1) were dissolved separately in a total of 3 g of toluene, mixed and aerated at 100° C. with 10 bar of synthesis gas (CO:$H_2$=1:1). After 30 minutes, the pressure was released, 3 g of 1-octene were added, and the mixture was hydroformylated for 4 hours at 100° C. and 10 bar. The conversion was 80%, the aldehyde selectivity was 95%. The molar ratio between n-nonanal and isononanal was 97:3.

The examples show that the proportion of n-aldehyde in the aldehydes obtained is significantly higher at a ligand-:metal molar ratio of at least 5 than at lower ligand:metal molar ratios.

We claim:

1. A process for the selective preparation of n-aldehydes in which at least one compound containing a vinyl or vinylidene group is reacted with carbon monoxide and hydrogen in the presence of a source of a metal from sub-group VIII and in the presence of a bidentate diphosphine ligand, where the diphos-phine ligand has the general formula I

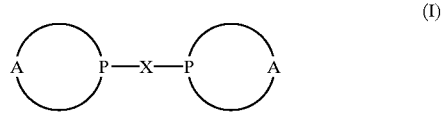

(I)

in which

A together with the phosphorus atom to which it is bonded, in each case forms a 2-phosphatricyclo [3.3.1.1{3,7}]decyl radical, in which one or more non-adjacent carbon atoms may be replaced by oxygen atoms and which is substituted or unsubstituted, and X is a bridging chain having 1 to 10 carbon atoms, and the molar ratio between the diphosphine ligand and the metal is at least 5.

2. A process as claimed in claim 1, where X is a $C_1$-$C_{10}$-al-kylene bridge, which may have one, two, three or four double bonds and/or may be interrupted by one, two or three non-adjacent heteroatoms and/or may be fused to one, two or three saturated or unsaturated 3- to 7-membered carbocyclic or heterocyclic rings.

3. A process as claimed in claim 1, where the molar ratio between the diphosphine ligand and the metal is at least 8.

4. A process as claimed in claim 2, where A, together with the phosphorus atom to which it is bonded, is a group of the general formula II

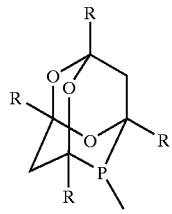

(II)

in which the radicals

R independently of one another, are alkyl, cycloalkyl, haloalkyl, aryl or aralkyl.

5. A process as claimed in claim 4, where the ligand is selected from
1,2-P, P'-di (2-phospha-1, 3,5,7-tetramethyl-6,9,10-trioxatricyclo[3.3.1.1{3,7}]decyl)ethane,
1,3-P,P'-di(2-phospha-1,3,5,7-tetramethyl-6,9,10-trioxatricyclo[3.3.1.1{3,7}]decyl)propane and
1,6-P,P'-di(2-phospha-1,3,5,7-tetramethyl-6,9,10-trioxatricyclo[3.3.1.1{3,7}]decyl)hexane.

6. A process as claimed in claim 1, where X is a three-atom chain.

7. A process as claimed in claim 1, where the compound containing a vinyl or vinylidene group is selected from $C_3$-$C_{20}$-$\alpha$-alkenes, isobutene, $\omega$-nitrilo-$C_2$-$C_{20}$-alkenes and O-alkoxycarbonyl-$C_2$-$C_{20}$-alkenes.

8. A process as claimed in claim 1, where the metal from sub-group VIII is rhodium.

* * * * *

UNITED STATES PATENT AND TRADEMARK OFFICE
CERTIFICATE OF CORRECTION

PATENT NO. : 6,753,450 B2
DATED : June 22, 2004
INVENTOR(S) : Ahlers et al.

It is certified that error appears in the above-identified patent and that said Letters Patent is hereby corrected as shown below:

<u>Column 10,</u>
Line 14, "O-alkoxycarbonyl-$C_2$-$C_{20}$-alkenes" should read -- $\omega$-alkoxycarbonyl-$C_2$-$C_{20}$-alkenes --.

Signed and Sealed this

Fourteenth Day of June, 2005

JON W. DUDAS
*Director of the United States Patent and Trademark Office*